United States Patent [19]
Kluge et al.

[11] Patent Number: 5,641,758
[45] Date of Patent: Jun. 24, 1997

[54] CYTARABINE DERIVATIVES, THE PREPARATION AND USE THEREOF

[76] Inventors: Michael Kluge, Am Huebaum 14, D-67169 Kallstadt; Herbert Schott, Hartmeyerstrasse 14, D-75400 Ludwigshafen, both of Germany

[21] Appl. No.: 335,090

[22] Filed: Nov. 7, 1994

Related U.S. Application Data

[63] Continuation-in-part of Ser. No. 133,018, Nov. 10, 1993, abandoned.

[51] Int. Cl.⁶ .............................. A61K 31/70; C07H 19/09
[52] U.S. Cl. .......................... 514/49; 514/908; 536/27.4; 536/28.5
[58] Field of Search .................. 536/27.4, 28.5; 514/49, 50, 908

[56] References Cited

U.S. PATENT DOCUMENTS

| | | | |
|---|---|---|---|
| 3,894,000 | 7/1975 | Wechter et al. | 514/49 |
| 4,022,963 | 5/1977 | Deutsch. | |
| 4,772,594 | 9/1988 | Hashimoto et al. | 514/50 |

FOREIGN PATENT DOCUMENTS

| | | |
|---|---|---|
| 8903837 | 5/1989 | WIPO. |
| 8903838 | 5/1989 | WIPO. |
| 9213561 | 8/1992 | WIPO. |

OTHER PUBLICATIONS

Schott et al., Liebigs Annalen der Chemie, vol. 1994, No. 5, pp. 465–470, May 1994.

Schwendener et al., Biochimica et Biophysica Acta., vol. 1026, pp. 69–79.

Divakar et al., J. of Chemical Society, Perkins Translation I, pp. 1171–1176, (1982).

Primary Examiner—James O. Wilson
Attorney, Agent, or Firm—Steinberg, Raskin & Davidson, P.C.

[57] ABSTRACT

Novel cytarabine derivatives of the formula

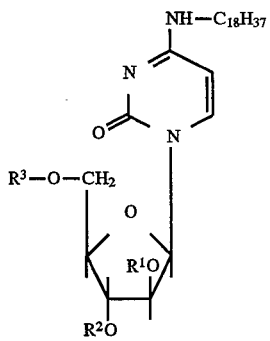

where $R^1$, $R^2$ and $R^3$, which can be identical or different, are each selected from the group consisting of hydrogen, aliphatic $C_2$–$C_5$-acyl, benzoyl or carboxy-$C_1$–$C_3$-alkylcarbonyl are described. The compounds are suitable for use directly or in the form of immunoliposomes for controlling diseases. Methods of preparing the novel cytarabine derivatives are also disclosed.

12 Claims, No Drawings

CYTARABINE DERIVATIVES, THE PREPARATION AND USE THEREOF

CROSS-REFERENCE TO RELATED APPLICATION

This application is a continuation-in-part of U.S. Patent Application Ser. No. 08/133,018, filed Nov. 10, 1993, now abandoned.

BACKGROUND OF THE INVENTION

The present invention relates to novel cytarabine derivatives, the preparation thereof and the use thereof for controlling diseases.

AraC (=cytarabine=4-amino-1-β-D-arabinofuranosyl-2 (1H)-pyrimidinone or 1-β-D-arabinofuranosyl-cytosine, Merck Index 11th Edition, No. 2790) is a cytostatic agent of proven use in the chemotherapy of cancers. However, AraC rapidly undergoes deamination by the cytosine deaminase present in the body and thus becomes inactive. To achieve a therapeutic effect it must therefore be administered in high doses which are associated with unpleasant side effects for the patient.

In order to delay the rapid enzymatic deamination, the amino group of the cytosine residue has been provided with acyl protective groups (Int J. Cancer 37 (1986) 149). The cytostatic effect of the resulting $N^4$-acyl AraC derivatives is, however, even when they are administered in the form of liposomes, no better than that of underivatized AraC. The $N^4$-acylamide linkage of these AraC prodrugs is able to delay enzymatic deamination in vivo for only a short time.

SUMMARY OF THE INVENTION

We have now found novel cytarabine derivatives in which the cytarabine is more effectively protected against enzymatic deamination.

The present invention relates to cytarabine derivatives of the formula I

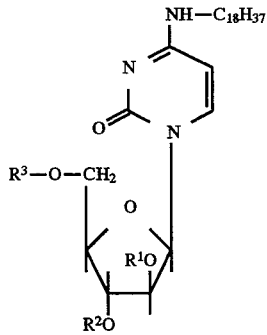

where $R^1$, $R^2$ and $R^3$, which can be identical or different, are each hydrogen, aliphatic $C_2$–$C_5$-acyl, benzoyl or carboxy-$C_1$–$C_3$-alkylcarbonyl. The radical derived from succinic acid may be particularly mentioned for $R^1$, $R^2$ and $R^3$.

The novel cytarabine derivatives of the formula I can be prepared by reacting a compound of the formula II

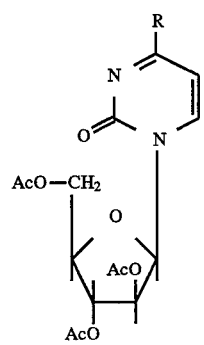

where Ac is acetyl and R is chlorine or

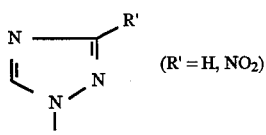

($R' = H, NO_2$)

with octadecyl amine; and subsequently, where appropriate, replacing acetyl radicals in the resulting compound by $R^1$, $R^2$ or $R^3$.

The reaction takes place well in a polar solvent such as dioxane or methanol at the boiling point.

Replacement of the acetyl radicals by hydrogen or other acyl radicals can be carried out as follows:

The acetyl radicals are replaced by hydrogen by ammonolysis by standing in aqueous or methanolic ammonia at 20°–60° C. for 2–24 hours. The hydrogens in the resulting compounds are subsequently replaced by acyl radicals by reaction with appropriate carboxylic anhydrides or carbonyl chlorides. The reaction takes place well in pyridine at room temperature.

The starting materials required for the reaction are known substances (J.C.S. Perkin I (1982) 1171) or can be prepared by known processes.

The novel compounds are distinguished from AraC by improved deaminase resistance. Because of their amphiphilic properties, they can easily be converted into aqueous pharmaceutical forms. It is furthermore possible, surprisingly, to modify within wide limits the amphiphilic properties of the AraC derivatives according to the invention by the number, length, nature and position of each of the substituents. The amphiphilic AraC derivatives are thus soluble in aqueous buffer systems and/or dispersible in the form of liposomes. All conventional processes for preparing liposomes can be used to form the liposomes, such as ultrasound, gel chromatography or detergent dialysis. The lipophilic radicals introduced in each case also have a crucial influence on the size and stability of the liposomes formed from the amphiphilic AraC derivatives together with other lipid components.

However, it is possible by targeted introduction of lipophilic radicals not only to control in a targeted manner the amphiphilic nature of the AraC derivatives according to the invention but, surprisingly, also crucially to optimize the cytostatic effect of AraC.

The novel compounds can be employed, like AraC itself, for malignant diseases of the hemopoietic cells, especially for acute leukemias and chronic myeloid leukemia in blast crisis.

The cytostatic effect of the amphiphilic AraC derivatives can, surprisingly, be used in immunoliposomes for targeted destruction of certain tumor cells. To do this, the amphiphilic AraC derivatives are dispersed together with other functionalized lipid components in the form of liposomes in physiological buffer systems.

Monoclonal antibodies are immobilized on the functional groups on the liposome membrane. The resulting immunoliposomes are in vitro preferentially taken up by the tumor cells which express the antigen corresponding to the antibody. The result of this cell targeting is the selective destruction of the particular target tumor cell in a mixture of different cells.

The effect of the novel compounds can be shown in the following design of experiment:

Leukemia was simulated in DBA/2 mice by intravenous injection of L1210 tumor cells. On days 3 and 7 after injection of the tumor cells, the tumor-bearing animals received various doses of the test substance or solvent. The test substance was a liposome preparation of 4-(1-octadecylamino)-1-β-D-arabinofuranosyl-2(1H)-pyrimidinone. The solvent was PBS—(phosphate buffered saline). The experimental groups comprised the following:

Control group (solvent)
i.v. administration (2 doses)
i.p. administration (2 doses)
i.v. AraC as reference (2 doses)
i.p AraC as reference (2 doses)

The result of the treatment was assessed by calculating the median survival time in each of the experimental groups (10 animals in each group).

In these experiments, the novel compounds showed a better effect than AraC.

The novel compounds are intended to be employed in a dose of about 40–1,000 mg per patient per day.

DETAILED DESCRIPTION

EXAMPLE 1

Preparation of 4-(1-octadecyl)-β-D-arabinofuranosyl-2(1H)-pyrimidinone

Octadecylamine (19.0 mmol, 5.1 g) was dissolved in 40 ml of ethanol and added dropwise, with stirring, to 50 ml of dioxane wherein 5.0 g (11.9 mmol) of 4-(1,2,4-triazol-1-yl)-1-β-D-2', 3', 5'-tri-O-acetylarabinofuranosyl-2 (1H)-pyrimidinone were dissolved. The reaction mixture was then refluxed with heating for 1 hour, concentrated to a syrup which was dissolved in chloroform and chromatographed on a silica gel column (10×9 cm). The column was first eluated with one liter of chloroform. Then, the desired reaction product (the first three UV-active products having the highest $R_f$ values) was eluated from the column with three liters of chloroform/methanol (90:10). The concentrated eluate was deacetylated and again concentrated to a syrup from which the product crystallized after addition of methanol. This yielded 85% or 5.0 g of the title compound (m.p. 159° C.) as white powder.

$C_{27}H_{49}N_3O_5$ (495.7):

calculated: C 65.42, H 9.96, N 8.48;
found: C 65.43, H 10.35, N 8.49.

EXAMPLE 2

Preparation of 4-(1-octadecyl)-1-β-D-arabinofuranosyl-2(1H)-pyrimidinone 60 g (142 mmol) of 4-(1,2,4-triazol-1-yl)-1-β-D-2', 3', 5'-tri-O-acetylarabinofuranosyl-2 (1H)-pyrimidinone were dissolved in 450 ml of dry dioxane. A solution of 59 g (221 mmol) of 1-octadecylamine dissolved in 450 ml of ethanol was added dropwise to this solution. The mixture was then refluxed for 2 hours and subsequently cooled. The solvent was stripped off under reduced pressure and the remaining syrup was dissolved in 750 ml of methanol saturated with ammonia. The solution was left at room temperature for about 12 hours, during which the required product gradually precipitated. To complete the crystallization, the mixture was stored at –20° C. for some time. The precipitate was then filtered off with suction, washed with diethyl ether and dried in an oven at about 60° C. The resulting crude product (about 60 to 70 g) was recrystallized from 80% strength aqueous methanol. This resulted in 70 g of 4-(1-octadecylamino)-1-β-D-arabinofuranosyl-2(1H)-pyrimidinone as white crystalline product which had an $R_f$ of 0.43 on silica gel in the system chloroform/methanol 4:1 (v:v).

EXAMPLE 3

Preparation of 4-(1-octadecylamino)-1-β-D-5'-O-succinoyl-arabinofuranosyl-2(1H)-pyrimidinone 2.3 g (4.3 mmol) of 4-(1-octadecylamino)-1-β-D-arabinofuranosyl-2(1H)-pyrimidinone were dissolved in 10 ml of dry pyridine, and 0.7 g (5.7 mmol) of 4-dimethylamino-pyridine and 0.7 g (7 mmol) of succinic anhydride were added. The mixture was stirred at room temperature for about 12 hours and then chromatographed on a cation exchange column (LEWATIT, pyridinium form) with pyridine/water 1:4 (v:v). The eluate was concentrated under reduced pressure to a syrup which was then evaporated several times with toluene. The resulting foam was dissolved in a little chloroform and fractioned on a silica gel column with chloroform/ethanol mixtures in which the ethanol content was increased stepwise from 10% to 100%. The fractions with the required product, which came off the column at high ethanol contents, were combined and concentrated under reduced pressure to a syrup. The syrup was dissolved in chloroform and precipitated in an excess of an ether/hexane mixture (3:2; v:v). HPLC on a $C_{18}$ reverse phase removed the 2', 3' isomers which occurred as by-products. Fractions which contained the required product were concentrated to give 4-(1-octadecylamino)-1-β-D-5'-O-succinoylarabinofuranosyl-2(1H)-pyrimidinone as white powder which had an $R_f$ of 0.47 on silica gel in the system chloroform/ethanol 4:1 (v:v).

EXAMPLE 4

Preparation of Liposome Products

To prepare the liposome dispersion, the following were dissolved per ml of 1/1 chloroform/methanol (v/v): 100 mg of soybean phosphatidylcholine, 10 mg of cholesterol, 1 mg of α-tocopherol, 7 mg of $N^2$-palmitoyl-$N^6$-succinoyl-L-lysine and 12 mg of 4-(1-octadecylamino)-1-β-D-arabinofuranosyl-2(1H)-pyrimidinone. 0.6 ml of this stock lipid solution was converted into a lipid film in a test tube by blowing in air, and the film was then dried at 50° C. under reduced pressure for about 1 hour. 3 ml of 10 mM PBS (0.9% NaCl and 10 mM $NaH_2PO_4$, pH 7.3) were added to the film, and the mixture was sonicated using the microtip of a disintegrator at 40 watt for 30 minutes. This resulted in an opalescent liposome dispersion which was used for the following reaction.

EXAMPLE 5

Preparation of Immunoliposomes 1.2 nmol of an antibody as lyophilisate were mixed with 50 µl of the liposome product from Example 4 and 7 mg (27 µmol) of N-(3-dimethylaminopropyl)-N'-ethylcarbodiimide×HCl (EDC) and adjusted to pH 4 by adding 30 µl of PBS. Two further 7 mg portions of EDC were added at intervals of one hour. After the reaction mixture had been stirred at room temperature for about 5 hours, it was loaded onto an ULTROGEL ACA 22 column and fractionated with PBS (pH 7.4). Fractions whose absorption ratios agreed with the values for the liposome product employed were combined and used for the cell targeting.

EXAMPLE 6

In Vitro Antitumor Activity of 4-(1-octadecylamino)-β-D-arabinofuranosyl-2(1H)-pyrimidinone In vitro, the cytotoxicity of 4-(1-octadecylamino)-1-β-D-arabinofuranosyl-2(1H)-pyrimidinone prepared according to Example 1 or 2 was tested in a panel of human tumor cell lines using the MTT (=[3-(4,5-dimethylthiazol-2-yl)-2,5-diphenyl-tetrazolium bromide) dye reduction assay described by Mosmann (Mosmann, T. 1983 Rapid colorimetric assay for cellular growth and survival: Application of proliferation and cytotoxicity assays, J. Immunol. Meth. 65, 55–63).

The $IC_{50}$ values for 4-(1-octadecylamino)-1-β-D-arabinofuranosyl-2(1H)-pyrimidinone (NOAC) and those for 1-β-D-arabinofuranosyl-2(1H)-pyrimidinone (ara-C) as comparison are summarized in Table 1.

TABLE 1

In vitro cytotoxicity of 4-(1-octadecylamino)-1-β-D-arabinofuranosyl-2(1H)-pyrimidinone (NOAC) in comparison to ara-C

| Tumor cells | $IC_{50}$ NOAC (µM) | $IC_{50}$ ara-C (µM) |
|---|---|---|
| HL-60 | <50 | >200 |
| U937 | <100 | >200 |
| K562 | <200 | >400 |
| CCRF-CEM | 50 | <1 |
| CCRF-CEM (dcK)$^{-1}$ | <140 | >550 |

[1]: Deoxycytidine kinase (dCK$^-$) deficient cell line

EXAMPLE 7

In Vivo Antitumor Activity on L1210 Murine Leukemia

The anti-tumor activity of the liposomal drug preparations was evaluated with the murine L1210 leukemia model in female BDF1 mice (Rubas et al., Int. J. Cancer, 37, 149–154 (1986)). The L1210 cells ($1 \times 10^5$) from donor ascites were injected i.v.

Groups of 5–6 mice were treated with a liposomal preparation of 4-(1-octadecylamino)-1-β-D-arabinofuranosyl-2 (1H)-pyrimidinone (NOAC) prepared according to Example 4 or 4-(1-hexadecylamino)-1-β-D-arabinofuranosyl-2(1H)-pyrimidinone ($N^4$-hexadecyl-ara-C). Control groups of 5–6 mice received ara-C dissolved in phosphate buffer (PB). The animals were observed daily until death or 60 days. Increase in lifespan of the treated animals (T) was compared to that of the untreated controls (C), expressed as T/C in percentages. Animals surviving 60 days were included in the calculation and considered as being cured.

a) The results as obtained upon intravenous drug application are summarized in Table 2

TABLE 2

Intravenous treatment of L1210 leukemia in BDF1 mice after intravenous implantation of L1210 cells

| Preparation | Total Dose | | Survival Time (days) | | T/C[1] | Survivors |
|---|---|---|---|---|---|---|
| | µmol/kg | mg/kg | Range | Mean ± SD | % | 60 Days |
| NOAC | 100 | 50 | >60 | 60 | 857 | 6/6 |
|  | 50 | 25 | 13.->60 | 52.1 ± 19.2 | 744 | 5/6 |
| Ara-C in PB[2] | 200 | 49 | 10.->60 | 19.8 ± 19.7 | 282 | 1/6 |
| $N^4$-Hexadecyl-ara-C | 100 | 48 | 11–16 | 12.0 | nd | 0/5 |
| " | 50 | 24 | 10–11 | 10.6 | nd | 0/5 |
| Controls | — | — | 7.0 | 7.0 | 100 | 0/6 |

[1]: Increase of lifespan T/C % calculated including 60d survivors. SD; standard deviation.
[2]: PB; phosphate buffer (67 mM, pH 7.4).

The results of Table 2 illustrate the superiority of NOAC over the prior art compounds, ara-C and $N^4$-hexadecyl-ara-C.

b) The results as obtained upon oral drug application are summarized in Table 3.

TABLE 3

Cytostatic effect of 4-(1-octadecylamino)-1-β-D-arabinofuranosyl-2(1H)-pyrimidinone (NOAC) in liposomes after therapy on days 1–5 after intravenous L1210 inoculation

| Preparation | Total Dose | | Survival Time (days) | | T/C[1] | Survivors |
|---|---|---|---|---|---|---|
| | mmol/kg | mg/kg | Range | Mean ± SD | % | 60 Days |
| NOAC | 1 | 496 | 23–>60 | 54 ± 15 | 673 | 5/6 |
| | 2 | 992 | 31–>60 | 55 ± 12 | 689 | 5/6 |
| Ara-C in PB | 2 | 486 | 10–52 | 13 ± 17 | 221 | 0/6 |
| Controls | — | — | | 7.2 ± 0.4 | 100 | 0/6 |

[1]: Increase of lifespan T/C %, calculated including 60 day survivors. SD; standard deviation.

EXAMPLE 8

In Vivo Activity on Human Tumor Xenografts in Nude Mice After Intraperitoneal Drug Application 6 to 8 week old nude mice of NMRI genetic background were used for all experiments. Tumors were implanted subcutaneously in both flanks of athymic nude mice. Treatment was started as soon as the tumors reached a median diameter of 6 mm, depending on the doubling time between day 12–42. Mice were randomly assigned to treatment groups and control group (5–6 mice per group bearing 6–12 evaluable tumors).

Tumor size was measured by two-dimensional measurement with calipers. The antitumor effect was evaluated following maximal tumor regression, in non-regressing tumors after 3–4 weeks. Relative tumor volume (RTV) values were calculated for each single tumor by dividing the tumor volume day×by the tumor volume day 0 at the time of randomization. Median RTV values were used for further evaluation.

Drug therapy was intraperitoneal on day 1,4,7 and 10. The dose of 150 mg/kg/day was considered to be the maximal tolerated dose resulting in a lethality of 14% in tumor-bearing nude mice.

Tumor growth inhibition was calculated according to relative tumor volume of control minus test divided by the control group. Furthermore the specific growth delay (SGD) was calculated with regard to the tumor doubling time (DT) by doubling time test group minus control divided by the doubling time of the control group.

Toxicity was assessed by lethality within 10 days after last therapy and body weight loss. The body weight of the nude mice was measured weekly, for rapidly growing tumor lines, measurements were done twice weekly. At the maximal tolerable dose the mice were allowed an $LD_{20}$ or a median body weight loss of 10–15% in the 2 weeks following the last injection.

The results are shown in Table 4.

TABLE 4

In vivo activity of 4-(-octadecylamino)-1-β-D-arabinofuranosyl -2(1H)-pyrimidinone in human tumor xenografts in the nude mouse

| Tumors | Type | Growth inhibition (%)[1] |
|---|---|---|
| Leukemias | | |
| Leukemia | HL-60 Acute promyelocytic leukemia | 97 |
| Leukemia | CCRF-CEM Acute lymphatic leukemia | 96 |
| Solid tumors | | |
| Mammary carcinoma | MAXF 401 Adenocarcinoma | 85 |
| Prostate carcinoma | PC3M Adenocarcinoma | 83 |
| Lung carcinoma | LXFS 605 small cell | 73 |
| Lung carcinoma | LXFL 529 large cell | 79 |
| Melanoma | MEXF 276 amelanotic | 39 |
| Ovary carcinoma | OVXF 1023 . . | 45 |

[1]: Tumor growth inhibition at maximal tolerable dose (MTD): 150 mg 4-(1-octadecylamino)-1-β-D-arabinofuranosyl-2-(1H)-pyrimidinone/kg/day.

What is claimed is:

1. A compound of the formula I

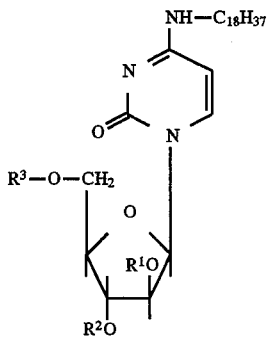

where $R^1$, $R^2$ and $R^3$, which are identical or different, and each is selected from the group consisting of hydrogen, aliphatic $C_2$-$C_5$-acyl, and carboxyl-$C_1$-$C_3$-alkylcarbonyl.

2. Process for preparing the compounds of claim 1, which comprises:

a) preparing a solution of a compound of formula II:

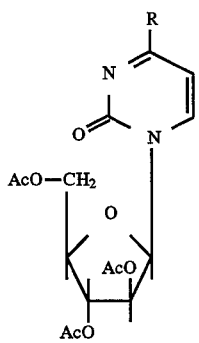

where Ac is acetyl and R is chlorine or

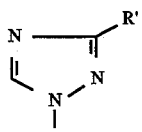

wherein R' is H or $NO_{O2}$;

b) adding a sufficient amount of octadecyl amine to the solution formed in step a) to form a reaction mixture;

c) heating the reaction mixture and isolating the product; and d) optionally replacing the acetyl radicals in the resulting product of step c) with $R^1$, $R^2$ and $R^3$, where $R^1$, $R^2$ and $R^3$ are identical or different and each is selected from the group consisting of hydrogen, aliphatic $C_2$-$C_5$-acyl, benzoyl, and carboxyl-$C_1$-$C_3$-alkylcarbonyl.

3. A pharmaceutical composition containing a compound of claim 1, included within immunoliposomes.

4. A method of treating malignant diseases of hemopoietic cells comprising administering an effective amount of a compound of claim 1 to a patient in need of such treatment.

5. The compound of claim 1, selected from the group consisting of 4-(1-octadecylamino)-β-D-arabinofuranosyl-2(1H)-pyrimidinone, and 4-(1-octadecylamino)-1-β-D-5'-O-succinoyl-arabinofuranosyl-2(1H)-pyrimidinone.

6. The pharmaceutical composition of claim 3, wherein said compound is selected from the group consisting of 4-(1-octadecylamino)-β-D-arabinofuranosyl-2(1H)-pyrimidinone, and 4-(I-octadecylamino)-1-β-D-5'-O-succinoyl-arabinofuranosyl-2(1H)-pyrimidinone.

7. The method of claim 4, wherein said compound is selected from the group consisting of 4-(1-octadecylamino)-β-D-arabinofuranosyl-2(1H)-pyrimidinone, and 4-(1-octadecylamino)-1-β-D-5'-O-succinoyl-arabinofuranosyl-2(1H)-pyrimidinone.

8. The method of claim 4, wherein said malignant diseases of hemopoietic cells comprise acute leukemias.

9. The method of claim 4, wherein said malignant disease of hemopoietic cells is chronic myeloid leukemia.

10. A method for treating a cytarabine-susceptible condition, comprising administering an effective amount of the compound of claim 1 to a patient in need thereof, wherein said condition is selected from the group consisting of leukemia, lung carcinoma, melanoma and ovary carcinoma.

11. The method of claim 4, wherein said effective amount is from about 40 to about 1,000 mg per day.

12. The method of claim 4, wherein said effective amount is administered within liposomes.

* * * * *